(12) United States Patent
Durkee et al.

(10) Patent No.: US 6,536,275 B1
(45) Date of Patent: Mar. 25, 2003

(54) ULTRASONIC TRANSDUCER FOR LIQUID MEASUREMENT

(75) Inventors: Scott Robert Durkee, New Haven, VT (US); Robert Downing LaClair, Richmond, VT (US)

(73) Assignee: Simmonds Precision Products, Inc., Charlotte, NC (US)

( * ) Notice: Subject to any disclaimer, the term of this patent is extended or adjusted under 35 U.S.C. 154(b) by 0 days.

(21) Appl. No.: 09/685,357

(22) Filed: Oct. 10, 2000

(51) Int. Cl.[7] .................. G01F 23/28; G01F 23/284; G01F 23/00
(52) U.S. Cl. .................. 73/290 V; 73/290 R
(58) Field of Search .................. 367/13, 141, 152; 84/DIG. 24; 600/459; 310/319, 334; 73/290 V

(56) References Cited

U.S. PATENT DOCUMENTS

| 4,297,607 | A | * | 10/1981 | Lynnworth et al. | .......... 310/334 |
| 5,343,443 | A | * | 8/1994 | Merewether | .......... 367/152 |
| 6,215,226 | B1 | * | 4/2001 | Durkee | .......... 310/319 |
| 6,236,142 | B1 | * | 5/2001 | Durkee | .......... 310/319 |

FOREIGN PATENT DOCUMENTS

| JP | 52031788 | * | 3/1977 |
| WO | WO99/32858 | | 7/1999 |

* cited by examiner

Primary Examiner—Hezron Williams
Assistant Examiner—Rodney T Frank
(74) Attorney, Agent, or Firm—David R. Percio; Calfee, Halter & Griswold LLP

(57) ABSTRACT

An ultrasonic transducer is disclosed comprising a layer of piezoresonator material capable of transmitting from a top surface thereof an ultrasonic pulse into a tank of liquid and receiving at the top surface reflections of the transmitted pulse from the liquid; and a matching layer of pure crystalline Boron Nitride disposed on the top surface. The pure crystalline Boron Nitride layer is operative to match the acoustic impedances of the piezoresonator material and the tank liquid about the operational frequency passband of the ultrasonic pulse. The ultrasonic transducer may be disposed in an assembly for measuring a quantity of liquid in the tank. The assembly comprises a housing having a top surface for interfacing with the liquid of the container; the ultrasonic transducer disposed therein, the top and bottom surfaces of the piezoresonator layer covered with layers of conductive material; and a lead wire for each surface of the piezoresonator layer connected at one end to the conductive material layer thereof, the lead wires connectable at the other ends to a transducer driver/receiver circuit. The matching layer of pure crystalline Boron Nitride disposed on the top surface of the piezoresonator layer is configured as a window between the piezoresonator layer and the liquid at the top surface of the assembly. A surface of the matching layer at the liquid interface is covered with at least one metal layer.

27 Claims, 8 Drawing Sheets

SECTION A-A (BACKGROUND)

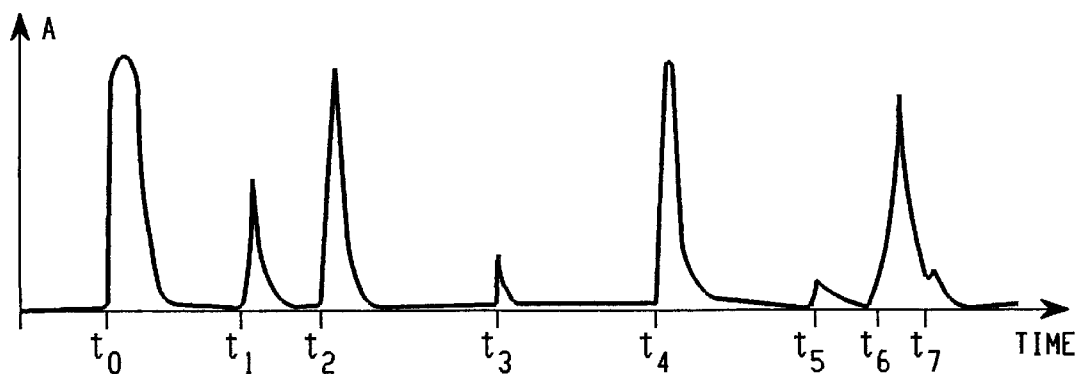
Fig. 7
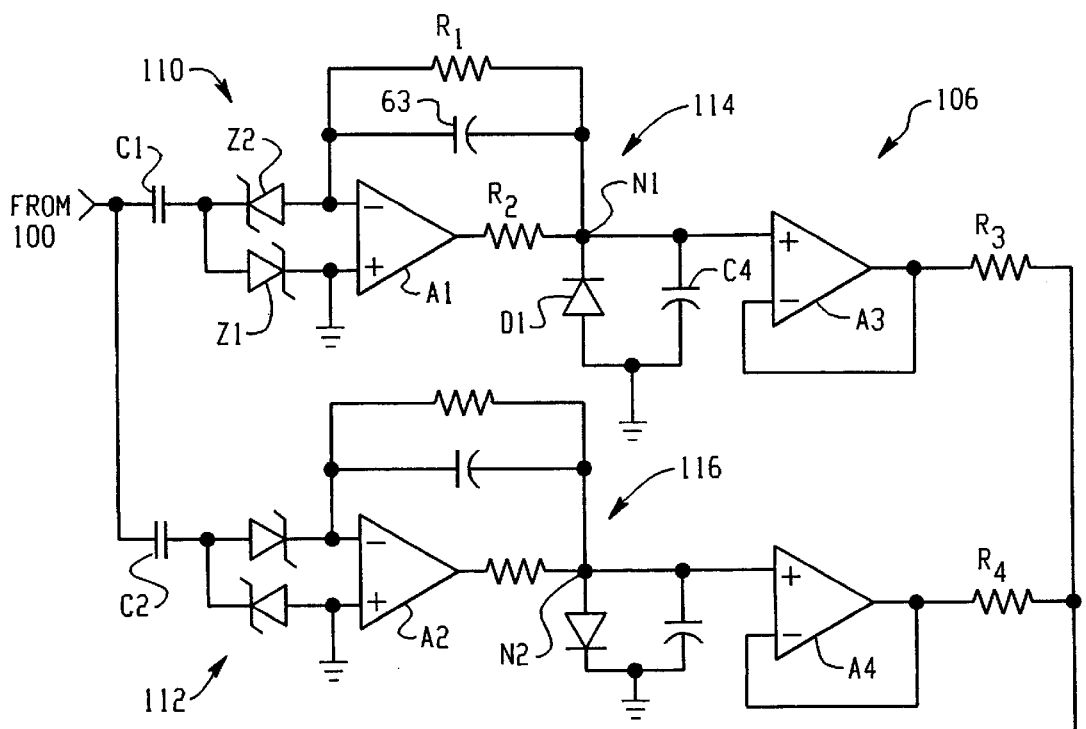
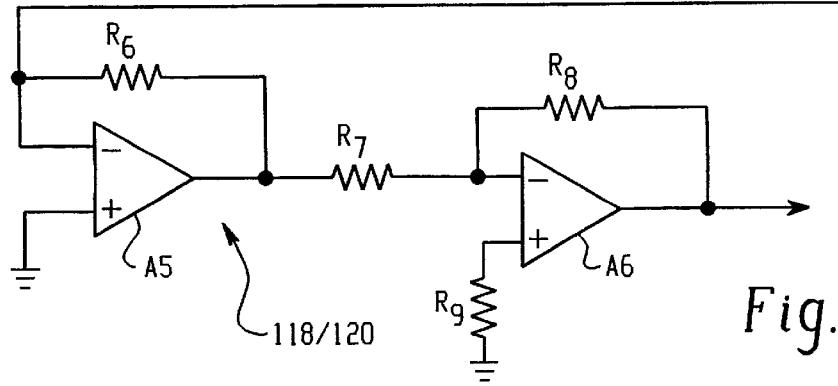
Fig. 8

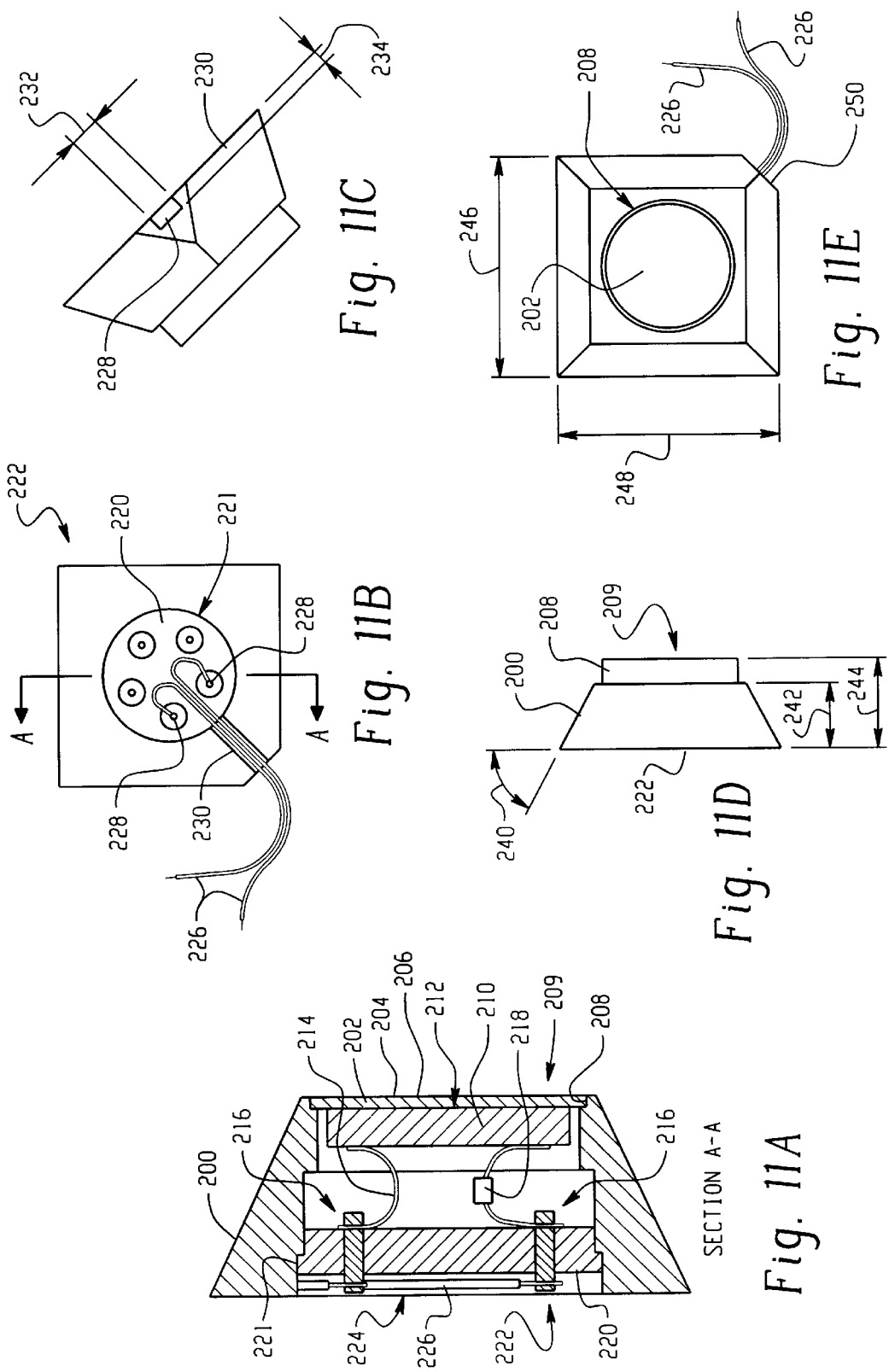

ULTRASONIC TRANSDUCER FOR LIQUID MEASUREMENT

BACKGROUND OF THE INVENTION

The present invention is directed to ultrasonic transducers, in general, and more particularly to an improved ultrasonic transducer for measuring ultrasonically the quantity of liquid in a tank.

Ultrasonic liquid gauging systems, like a fuel gauging system for an aircraft, for example, generally include one or more ultrasonic transducers at each fuel tank of the aircraft, generally disposed at the bottom thereof, and one or more target reflectors disposed in the tank at predetermined distances from the ultrasonic transducer. In operation, an incipient ultrasonic burst signal is transmitted from the transducer, conducted through the liquid, reflected from the height of the liquid, i.e. the liquid/air interface, and returned to the transducer where it is received. A round trip time period from inception to reception of the ultrasonic burst signal is measured to determine the height of the liquid in the tank. In order to determine liquid height the velocity of sound of the liquid is needed. One technique for determining velocity of sound of the liquid is to utilize the time measurements for the ultrasonic burst reflections from the one or more target reflectors in the tank. Since the distance between a target reflector and the transducer is known the velocity of sound may be determined from said distance and the time measurement for the target reflector.

But this presumes that the velocity of sound of the liquid is substantially constant over a large liquid height profile around the target reflector. Unfortunately, this may not always be the case, especially if the liquid in the tank is thermally stratified. Accordingly, having the velocity of sound at one height of the liquid may not be sufficient across the over all height profile of the tank liquid, especially if accuracy of liquid quantity measurement is of paramount importance. Thus, it would be an important improvement to be capable of determining the velocity of sound cumulatively at the height of the liquid in the tank under thermally stratified conditions.

In addition, stratification may also occur due to a separation of different liquids in the tank. For example, reflections which may occur from the stratified liquid levels, may compromise the time measurements of the reflections from the target reflectors. Therefore, a liquid gauging system may also be improved by distinguishing between the different reflections in order to obtain accurate time measurements from the reflections of the target reflectors.

Also, current ultrasonic transducers like that illustrated in cross sectional view in FIG. 3A, for example, include a bottom layer of piezoresonator material which is of a different acoustic impedance than that of the liquid in the tank about the operational frequency passband of the ultrasonic burst or pulse transmitted and received therefrom. In some cases, this difference in acoustic impedance between the piezoresonator material and liquid may be greater than thirty to one, for example. Generally, one or more layers of material are disposed between the piezoresonator material and the tank liquid for matching the acoustic impedances of the piezoresonator material and the tank liquid to render an efficient energy transfer. Such impedance matching techniques are proposed in the following U.S. patents: Merewether, U.S. Pat. No. 5,343,443, issued Aug. 30, 1994; Breimesser et al., U.S. Pat. No. 4,672,591, issued Jun. 9, 1987; Rhyne, U.S. Pat. No. 5,706,564, issued Jan. 13, 1998; Mitchell et al., U.S. Pat. No. 4,396,663, issued Aug. 2, 1983; Kikuchi et al., U.S. Pat. No. 5,438,999, issued Aug. 8, 1995; and Seyed-Bolorforosh et al., U.S. Pat. No. 5,553,035, issued Sep. 3, 1996.

However, this acoustic impedance matching has not always been accurate due primarily to the available material for use in the additional impedance matching layer or layers. For example, Merewether (U.S. Pat. No. 5,343,443) proposes an anisotropic material for use as its primary acoustic impedance matching layer. Merewether's anisotropic layer is a composite material of a polymer phenolic resin embedded with random oriented fibers of a particular material. Proposed materials for the fibers included quartz, graphite, carbon, Boron Nitride, and Silicon Carbide, for example. Focus appeared to be on having favorable coefficients of thermal expansion (CTEs) between layers, rather than overall efficiency in acoustic energy transfer through the transducer.

Layers made of composite material of a random oriented matrix are not homogeneous and include fibrous particles which tend to scatter, reflect back or dissipate acoustic energy and therefore, are very lossy. Also, such materials are very complex and difficult to manufacture; often resulting in inconsistent quality from one batch to another, and thus, not reliable. Also, the characteristics of such composite material are not consistent over a wide temperature range. In addition, the use of more than one layer for acoustic impedance matching tends to create further losses, especially in broadband applications. Accordingly, an improvement in efficiency of energy transfer can occur if the acoustic impedance matching is made more accurate than currently implemented.

The embodiment of the invention which will be described in a succeeding section ameliorates the aforementioned drawbacks, thus providing a more accurate and improved ultrasonic transducer for liquid measurement.

SUMMARY OF THE INVENTION

In accordance with one aspect of the present invention, an ultrasonic transducer comprises a layer of piezoresonator material having top and bottom surfaces and capable of transmitting from the top surface an ultrasonic pulse into a tank of liquid and receiving at the top surface reflections of said transmitted pulse from the liquid; and a matching layer of pure crystalline Boron Nitride disposed on the top surface of the piezoresonator layer, the ultrasonic pulse and reflections thereof conductible through the matching layer between the top surface of the piezoresonator layer and the tank liquid, the pure crystalline Boron Nitride layer operative to match the acoustic impedance of the piezoresonator material to the acoustic impedance of the tank liquid about the operational frequency passband of the ultrasonic pulse.

In accordance with another aspect of the present invention, an ultrasonic transducer assembly for measuring a quantity of liquid in a container comprises a housing having top and bottom surfaces, the top surface for interfacing with the liquid of the container; an ultrasonic transducer disposed in said housing and comprising: a layer of piezoresonator material having top and bottom surfaces and capable of transmitting from the top surface an ultrasonic pulse into the container of liquid and receiving at the top surface reflections of said transmitted pulse from the liquid, the top and bottom surfaces of the piezoresonator material covered with layers of conductive material; and a matching layer of pure crystalline Boron Nitride disposed on the top surface of the piezoresonator layer and configured as a window between the piezoresonator material and the liquid at the top surface of the assembly, the ultrasonic pulse and reflections thereof conductible through the matching layer between the top surface of the piezoresonator layer and the liquid, the matching layer operative to match the acoustic impedance of the piezoresonator material to the acoustic impedance of the liquid about the operational frequency passband of the ultrasonic pulse, a surface of the matching layer at the liquid interface being covered with at least one metal layer; and a lead wire for each surface of the piezoresonator layer connected at one end to the conductive material layer thereof, the lead wires connectable at the other ends to a transducer driver/receiver circuit.

BRIEF DESCRIPTION OF THE DRAWINGS

FIG. 7 depicts envelope response time waveforms of the incipient and echo burst signals exemplifying the operation of the embodiment described in connection with FIG. 2.

FIG. 8 is a circuit schematic of a phase discriminator circuit suitable for use in the embodiment of FIG. 2.

FIGS. 11A–11E illustrate through various views an ultrasonic transducer configured in a housing suitable for embodying the single matching layer aspect of the present invention.

PREFERRED EMBODIMENTS

Figure 1:
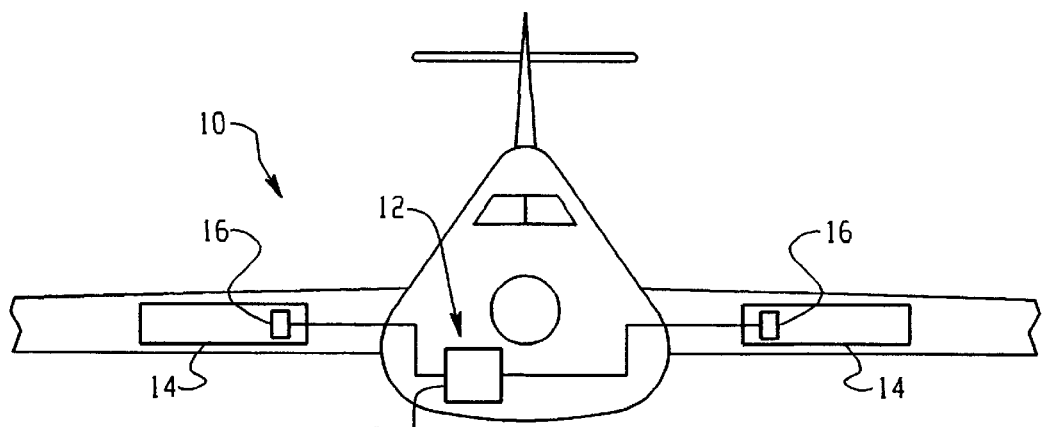
FIG. 1 is an illustration of an aircraft environment for a liquid quantity measurement or gauging system embodying one or more aspects of the present invention.

Referring initially to FIG. 1, an aircraft 10 is shown including a fuel quantity measurement or gauging system 12 in accordance with one or more aspects of the present invention. The fuel measurement system 12 is utilized to measure such fuel quantity parameters as: height of the liquid in a tank, and the volume and mass thereof for the aircraft fuel system. Although the invention is described herein primarily in the context of use within the aircraft 10, it will be appreciated that the invention may be used in non-aircraft applications as well, and with liquids other than aircraft fuel without departing from the scope of the invention. Accordingly, the fuel measurement system 12 can be used in virtually any application which requires liquid gauging in a tank.

The aircraft 10 includes a fuel system comprising one or more fuel tanks 14 which may contain aircraft fuel for operating the aircraft. For example, the aircraft 10 may have a tank 14 in each wing as represented in FIG. 1. It will be appreciated, however, that in another embodiment there may be several tanks 14 distributed throughout the aircraft 10. Included at each tank 14 are one or more sensors (collectively designated 16) which provide sensor data of fuel properties to a fuel measurement processor 18 wherein and from which the quantity of fuel contained in each tank 14 may be determined, the disposition of such sensors being described below in more detail. The measurement processor 18 including an interface circuit together with the sensors 16 is all considered part of the fuel measurement system 12.

Figure 2:
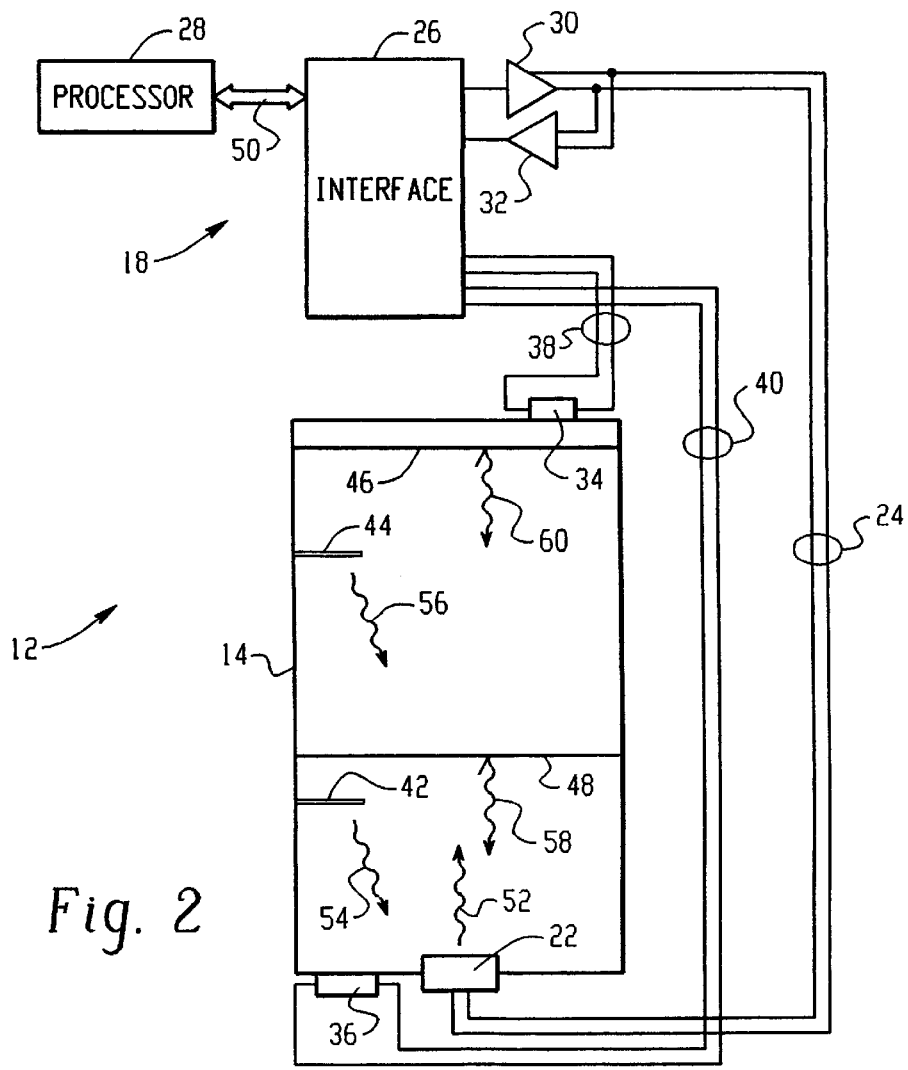
FIG. 2 is an illustration of an exemplary liquid measurement system embodiment suitable for use in the aircraft of FIG. 1.

FIG. 2 depicts a more detailed illustration of the fuel measurement system 12 including the measurement processor 18 and an exemplary fuel tank 14. Referring to FIG. 2, an ultrasonic transducer 22, which will be described in greater detail herebelow, is disposed at the bottom of the fuel tank 14 and may have one surface thereof in contact with the fuel in the tank 14 and another surface in contact with the outside environment. The transducer 22 is coupled over a pair of wires 24 to an interface circuit 26 of a processor 28 via data bus 50. The interface circuit 26 includes an ultrasonic driver circuit 30 and an ultrasonic receiver circuit 32 which couples the wire pair 24 thereto. The system 12 further includes temperature measuring sensors 34 and 36 which may be thermistors, for example. For the present embodiment, the thermistor 34 may be disposed at the top of the fuel tank for measuring the ullage or liquid surface temperature and the thermistor 36 may be disposed at the bottom of the fuel tank for measuring the temperature of the fuel thereat. Thermistors 34 and 36 are also coupled to the interface circuit 26 over wire pairs 38 and 40, respectively.

The fuel tank 14 includes target reflectors 42 and 44 which are located at known distances away from the ultrasonic transducer 22 or the bottom of the tank 14. For the present embodiment, the distances of 42 and 44 are 0.30 and 0.80 of the height of the fuel when the tank 14 is considered full which is shown at 46. But, it is understood that more than two target reflectors may be used in an alternate embodiment or other distance values choosen for the target reflectors without deviating from the present invention The tank 14 may include a different liquid than the aircraft fuel, like water, for example, which may create a second interface 48 at the point of separation between the two liquids.

For the purposes of the present embodiment, the processor 28 may be a digital processor of the type manufactured by Intel Corporation bearing the model i486, for example, the operation of which being well known to all those skilled in the pertinent art. In addition, the interface circuit 26 may be similar to the type described in the copending U.S. patent application Ser. No. 08/997,271, entitled "Universal Sensor Interface", filed on even date herewith, and assigned to the same assignee as the instant application, which application being incorporated by reference herein to provide further structural and operational details thereof. Further details of the ultrasonic transducer 22 and driver and receiver circuits 30 and 32 will be provided in the following paragraphs.

In operation, the processor 28 under programmed control may provide signals over the digital bus 50 to the interface circuit 26 to excite the ultrasonic transducer 22 via driver circuit 30 to transmit an incipient ultrasonic burst or pulse waveform 52 at the desired ultrasonic frequency which may be on the order of one megahertz, for example. The ultrasonic transducer 22 receives ultrasonic burst echoes or reflections illustrated at 54 and 56 from the targets 42 and 44, respectively. The ultrasonic transducer 22 will also receive reflections from the interface layer 48 illustrated at 58 and a reflection illustrated at 60 from the height of the liquid or liquid surface 46. These ultrasonic echoes or reflections are converted to electrical signals by transducer 22 and conducted over the wire pair 24 back to the interface circuit 26 through the receiving circuit 32 and detected by the processor 28. The processor 28 may determine the timed relationship between the incipient ultrasonic burst 52 and its corresponding reflections 54, 56, 58 and 60 and store them in a memory thereof. The processor 28 may also read the temperature measurements of the thermistors 34 and 36 through the interface 26 where they are converted to digital representations and conducted over the bus 50. The digital representations of the temperature measurements of 34 and 36 may also be stored in a memory of the processor 28 for further processing therein which will become more evident from the description of a method of height determination ultrasonically for a thermally stratified fuel or liquid infra.

Figure 3A:
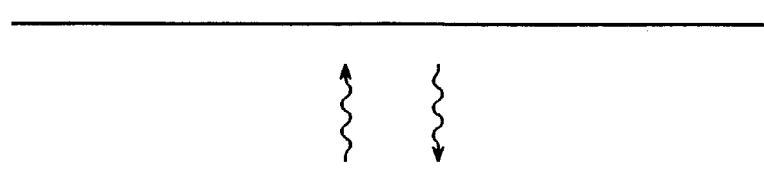
FIG. 3A is a cross sectional illustration of an ultrasonic transducer used for background purposes.
Figure 3B:
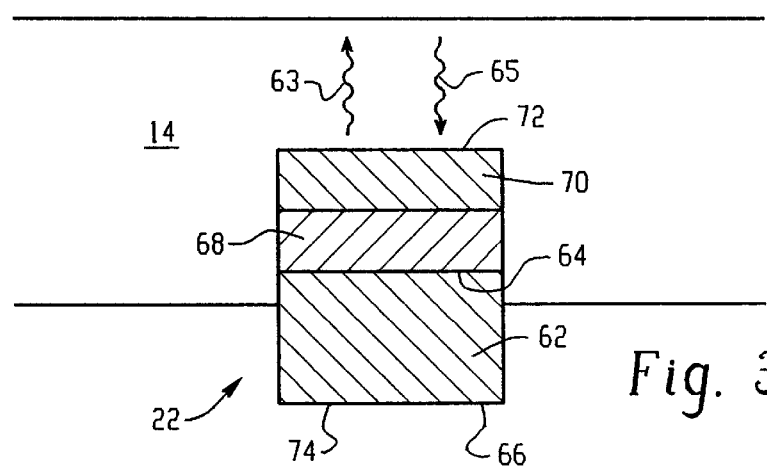
FIG. 3B is a cross sectional illustration of an embodiment of an ultrasonic transducer suitable for use in the liquid measurement system embodiment of FIG. 2.

A cross sectional illustration of an embodiment of an ultrasonic transducer suitable for use in the fuel measurement system 12 of FIG. 2 is shown in FIG. 3B. The ultrasonic transducer 22 includes a first layer 62 of a piezoresonator material having top and bottom surfaces 64 and 66, respectively. The transducer 22 further includes a second layer of material 68 disposed on the top surface 64 and having a thickness of approximately one-quarter wavelength, which is based on the frequency of the ultrasonic burst or pulse and the velocity of sound through the second layer of material. Still further, the transducer 22 includes a third layer of material 70 disposed on top of the second layer 68 and having a thickness of approximately one-quarter wavelength, which is based on the frequency of the ultrasonic pulse and the velocity of sound through the third layer of material.

Figure 3C:
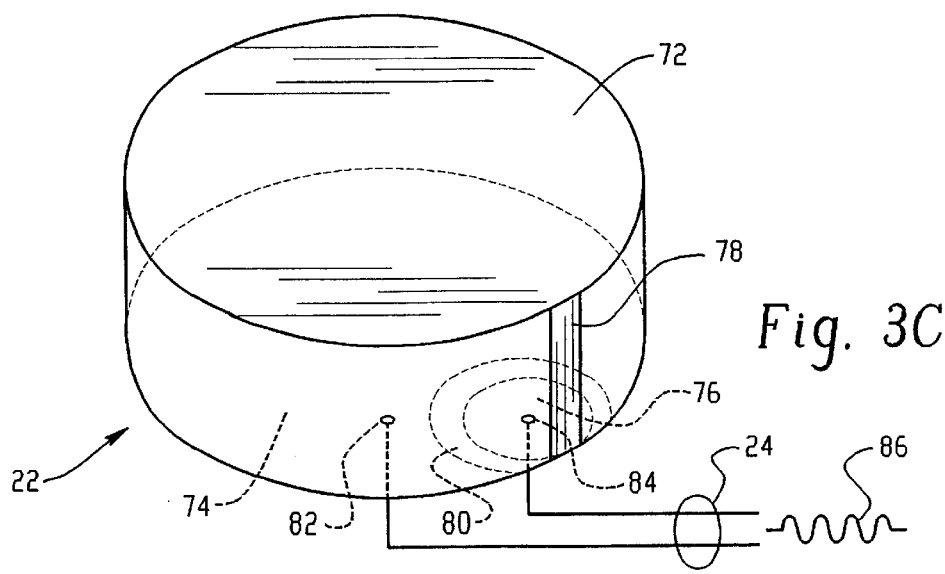
FIG. 3C is a sketch of an ultrasonic transducer shaped as a disk having its top and bottom surfaces coated with an electrically conductive material.

The ultrasonic transducer 22 may be shaped as a disc as shown in the illustration of FIG. 3C and may have its top and bottom surfaces coated with an electrically conductive material which may be Silver, for example, and which may be fired on to the ceramic material. The conductive material 72 on the top side of the transducer may be joined electrically with a small island of conductive material 76 at the bottom of the transducer 22 by a small conductive path of conductive material disposed along the thickness of the transducer as illustrated at 78. The island of conductive material 76 at the bottom surface is electrically isolated as shown at 80 from the bottom conductor 74 by the bottom non-conducting ceramic material itself. The wire pair 24 makes contact with the conductive regions 74 and 76 at contacts 82 and 84, respectively.

When electrically excited by an electrical pulse, illustrated at 86, over the wire pair 24, the transducer 22 transmits from the top surface 64 an ultrasonic pulse 63 which may be of a frequency of approximately one megahertz into the tank of liquid 14 and receives reflections 65 of the incipient pulse from the liquid at the surface 64 which are reconverted by the transducer 22 to electrical signals and conducted back over signal lines 24 to the processor 28 via the receiving circuit 32 and interface 26. The ultrasonic pulse 63 and reflections 65 thereof are conductible through the second and third layers 68 and 70, respectively, between the top surface 64 and the tank liquid To render an efficient energy conversion, the materials of the second and third layers 68 and 70, respectively, are chosen to have corresponding acoustic impedances to match the acoustic impedance of the piezoresonator material 62 to the acoustic impedance of the tank liquid about the operational frequency passband of the ultrasonic pulse.

In the present embodiment, the first layer comprises a piezoceramic material, such as lead zirconate titanate having an acoustic impedance of approximately 31.3 megaryals. Also in the present embodiment, the acoustic impedances $Z2$ and $Z3$ of the second and third layers 68 and 70, respectively, are determined from a substantially flat responding transfer function, like a Butterworth function, for example, of the acoustic impedances of the first layer material $Z1$ and the tank liquid $Z$ about the operational passband of the ultrasonic pulse. In connection with this function, the acoustic impedance $Z3$ may be determined as a function of the product of the acoustic impedance of the first layer $Z1$ taken to a first predetermined power which may be 1/7, for example, and the acoustic impedance of the fuel $Z$ taken to a second predetermined power which may be 6/7, for example. Likewise, the acoustic impedance of the second material $Z2$ may be determined as a function of the product of $Z1$ taken to a third predetermined power which may be 4/7, for example, and the acoustic impedance of the fuel $Z$ taken to a fourth predetermined power which may be 3/7, for example. Typically the acoustic impedance of the fuel is one megaryal and the acoustic impedance of lead zirconate titanate of the first layer is typically 31.3 megaryals. Thus, based on the Butterworth function, the acoustic impedances $Z2$ and $Z3$ of the second and third layers are calculated to be 7.15 megaryals and 1.635 megaryals, respectively.

In the present embodiment, the material for the third layer having the aforementioned acoustic impedance is easily satisfied by many polyurethanes. However, it is preferred that the material of the second layer also include the characteristics of a low density and medium Youngs Modulus which is given by the following relationship:

$$Z2=((E/\rho)*((1-\rho)/(1+\gamma)(1-2\gamma)))^{1/2}$$

Where E=Youngs Modulus (Pascals), $\rho$=density (kg/m$^3$), $\gamma$=Poisson's Ratio.

There is only a very special class of materials which may satisfy both the above relationship and the acoustic impedance $Z2=6.5-7.5\times10^6$ Ryals and this class of materials includes graphite and boron nitride. It is preferred that the graphite and/or boron nitride layer be grown by pyrolytic chemical vapor deposition. Experimental results of these materials results in a 10 to 11 dB improvement over the current design exemplified as the embodiment of FIG. 3A in the Background section.

Moreover, Applicants have found that a single acoustic impedance matching layer of pure crystalline Boron Nitride, especially for use with a piezoresonator layer of ceramic material, such as lead zirconate titanate (PZT); for example, exhibits near optimum impedance matching characteristics to liquid fuel without a second matching layer. Although the theoretical efficiency of a two impedance matching layer design appears better than a single matching layer design, the acoustic losses in the second matching layer which may be of a polyurethane material, for example, effectively defeats any gains provided by the dual matching layers. Therefore, in actual practice, a single layer of pure crystalline Boron Nitride exhibits improved acoustic energy efficiency with a simplified construction. Applicants have further found that metallizing a Boron Nitride matching layer provides a complete shield against possible electromagnetic interference (EMI) and offers an effective mechanical attachment to a metal housing in which the ultrasonic transducer may be mounted as will become more evident from the embodiment description found herein below.

The pure crystalline Boron Nitride material used in the single matching layer embodiment described below is grown by a proprietary process of BVD products, Inc. of Hudson, N.H. using pyrolytic chemical vapor deposition techniques in which special gases are mixed in a chamber at very high temperatures in excess of 2000° C. The gases react with one another at such temperatures to form dust like particles that settle slowly in a highly ordered crystalline structure. In this process, the growth rate of the Boron Nitride is on the order of 0.001 inch/hour in which case, it could take 30 hours or so to grow a layer in excess of 0.030 inches. Generally, a layer of greater thickness than what is desired for the transducer is grown and then machined down to the correct thickness. This process is considered well controlled and predictable and offers quality repeatability from batch to batch. Also, Boron Nitride in a pure crystalline form is a very stable chemical matrix that is substantially chemically unreactive to almost everything.

In addition, the pyrolytically CVD grown Boron Nitride is matched to the coefficient of thermal expansion of the PZT ceramic material of the piezoresonator without the need of complex composite matrix materials or multiple layers such as proposed by Merewether in U.S. Pat. No. 5,343,443 referenced herein above. Moreover, in contrast to the proposed Merewether design, the single matching layer embodiment of the present invention is designed for a narrow-band ultrasonic transducer, preferably on the order of one megahertz, for example, in order to maximize acoustic energy transmission efficiency and minimize response to noise outside the operation frequency range. Thus, the embodiment is based on maximizing the efficiency of the transducer and not the linearity or impulse response as in the case of Merewether.

FIGS. 11A–11E illustrate through various views an ultrasonic sensor configured in a housing suitable for embodying the single matching layer aspect of the present invention. This embodiment has particular application to aircraft fuel tanks comprising a skin of composite material in which the housed sensor may be embedded. Although the ultrasonic sensor is depicted in a particular housed configuration in FIGS. 11A–11E, it is understood that the transducer may assume a variety of configurations depending on the application. Referring to the cross-sectional view of FIG. 11A, a housing 200 which may be of a shape of a truncated pyramid section with a small cylindrical segment on top of the truncated plane thereof, for example, may be fabricated from Invar 36 manufactured by Carpenter Technology of Reading, Pa. which is a nickel-iron alloy that has a coefficient of thermal expansion which closely matches that of glass/ceramics (approx. 1 ppm/deg F.). Note pure crystalline Boron Nitride has ceramic-like material properties and therefore will exhibit similar thermal expansion characteristics. The Invar 36 material is preferably chosen for the housing 200 because it accepts solder tinning well and is so prepped for joining with the metallized Boron Nitride acoustic window which will be described in greater detail below.

As mentioned above, a pure crystalline Boron Nitride acoustic window layer 202 of the housed ultrasonic transducer may have a thickness substantially of one-quarter waveleng which is based on the frequency of the ultrasonic pulse and the velocity of sound (VOS) through the layer 202. In the present embodiment, the window layer 202 is metallized with a layer of copper 204, for example, which is overplated with a thin layer of chromium 206. The copper layer 204 provides a solderable substrate for the soldering of the acoustic window 202 to the tinned Invar 36 housing 200 around the top periphery of the cylindrical portion 208 of the top 209 of the transducer housing. The chromium layer 206 protects the copper layer 204 from attack by the fuel which comes in contact with the window layer 206 (the fuel contains sulfur which may combine with the copper to form copper sulfate, for example). The chromium layer 206 also prevents the formation of oxides during the soldering process. Both the copper and chromium layers serve as a Faraday shield for EMI protection. The Boron Nitride acoustic window layer 202 is also soldered to the Invar 36 housing 200 to form a hermetic joint around the top periphery of 208.

The pure crystalline Boron Nitride layer or window 202 is bonded to a PZT crystal resonator layer 210 at the bonding interface 212 using EPO-TEK 353ND epoxy adhesive, for example, which is specially formulated for use with optics (glass/ceramics). It exhibits a low viscosity which helps to guaranty a thin bond line at the interface 212. It has a 200 degree C. temp rating (continuous) and is resistant to jet fuel. It's high temperature rating allows the bonded joint 212 to withstand autoclave temperatures encountered during a curing cycle of the composite material of the tank skin in which the housed sensor may be embedded.

Electrical interface with the PZT crystal 210 is accomplished by way of lead wires 214 affixed to corresponding wrap-around terminals 216. The crystal 210 is covered on its top and bottom surfaces with a conductive material, which may be accomplished by silver plating, for example. The bottom surface is attached to one of the lead wires 214 and a finger of plating extends from the plating of the top surface, wrapping around the edge of the crystal and forming a small, electrically isolated pad on the bottom surface for attachment to the other of the lead wires 214. The transducer lead wires 214 are soldered to the terminals 216. In series with one of the lead wires 214 is a 47 microHenry tuning inductor 218 which improves operational performance of the transducer. A 1 Mega-Ohm resistor (not shown in drawing) may also be wired in parallel with the two lead wires 214 to serve as a safety outlet for an unwanted voltage spike that could occur as a result of an impact with the PZT crystal (like the piezoelectric pushbutton starters used on gas grilles, for example). In the present embodiment, the PZT crystal 210 is a LTZ type 2 crystal that is 2 millimeters thick and 12.7 millimeters in diameter and designed for a one megahertz resonant frequency, for example.

A cylindrically shaped hermetic header 220 containing the connecting terminals 216 is soldered around a circular inner periphery 221 of the housing 200 at the rear 222 thereof thus creating a hermetic housed transducer package. A rear cavity 224 may be potted with high-temp epoxy to insulate electrical lead wires 226 which are soldered to the terminals 216 of the header 220. The lead wires 226 may be teflon coated copper, for example. As shown in FIG. 11B, the transducer lead wires 226 exit the housing at the rear 222 through epoxy filled holes 228 and are passed through a channel 230 on the rear surface 222. As shown by the view of FIG. 11C, the dimension 232 of each hole 228 may be on the order of 0.11 inches and the height 234 of the channel 230 may be on the order of 0.060 inches, for example. The lead wires are connected to a transducer driver circuit which will be more fully described herein below.

As shown by the cross-sectional view of FIG. 11D, the truncated pyramidal housing portion is tapered at an angle 240 from the plane of its rear surface 222 which may be on the order of 63°, for example, with a height dimension 242 on the order of 0.300 inches, for example. The overall height dimension 244 of the housing 200 including the cylindrical portion 208 is on the order of 0.420 inches, for example. A top view of the housed transducer is shown in FIG. 11E. In this view, the side dimensions 246 and 244 of the truncated pyramid may both be on the order of 1.00 inches and the diameter of the top cylindrical portion may be on the order of 0.620 inches, for example. The pyramidal housing 200 includes a chamfer cut of approximately 45° at one of its bottom corners 250 which may have a dimension of 0.18 inches, for example. The operation of the foregoing described embodiment will be much the same as that described for the embodiment of FIGS. 3B and 3C herein above.

Embodiments of the driver circuit 30 and receiver circuit 32 suitable for use in the system described in connection with FIG. 2 are shown schematically in FIG. 4. Currently in aircraft applications of ultrasonic fuel gauging systems, there are constraints on the drive voltage limits of the power supply rails V+ and V– and these are typically limited to plus and minus 15 volts. This drastically limits the power per unit time that can be transferred to the ultrasonic transducer 22 from a drive circuit, like 30, for example. Ideally to obtain a sharp well defined leading edge on the reflected ultrasonic burst echo energy as well as maintaining a good signal to noise ratio therefor, it is desired to transmit the total energy of the incipient ultrasonic burst as quickly as possible. Thus, the conventional method of launching more energy by simply increasing the total length of time that the transmit burst is active quickly runs up against limitations, e.g. the echo pulses returned with the same low amplitude but of longer duration doing little for the signal to noise ratio. Accordingly, it is preferred to deliver the peak-to-peak sinusoidal ultrasonic burst well in excess of the power supply rails and hence transfer power at a much faster rate. The embodiment of FIG. 4 satisfies this desire.

Figure 4:
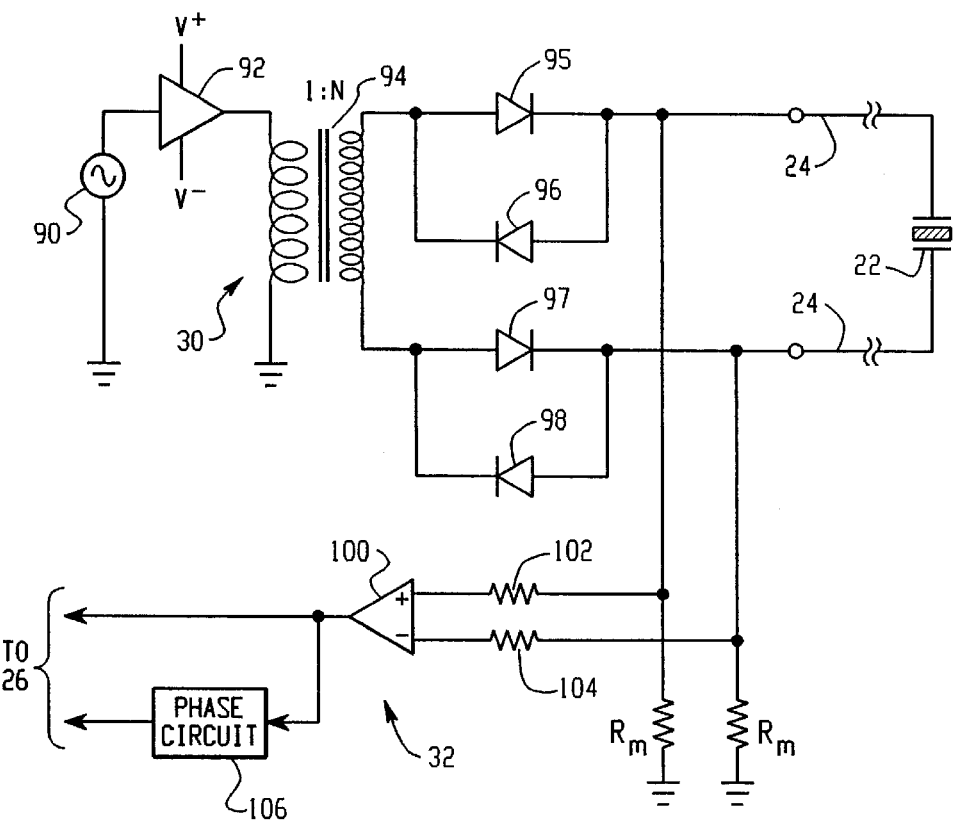
FIG. 4 is a schematic illustration of a circuit embodiment suitable for exciting an ultrasonic transducer and for receiving echo signals therefrom.

Referring to FIG. 4, the sinusoidal burst exciter illustrated at 90 may be embodied by the processor 28 and/or interface circuit 26 which is described in greater detail in the co-pending application Ser. No. 08/997,271. The electrical excitation signal generated from exciter 90 is coupled to an amplifier 92 which drives a conventional step up transformer 94 which has a winding ratio of 1:N from primary to secondary. The primary side of the transformer 94 may be connected to ground. The secondary side of transformer 94 is couple differentially to the transducer 22. More specifically, one end of the secondary side of transformer 94 is coupled through parallel, back to back diodes 95 and 96 to one of the pair of wires 24 leading to one side of the transducer 22. The other side of transducer 22 is coupled through the other wire of the pair 24 to another parallel back to back set of diodes 97 and 98 to the other side of the secondary of transformer 94. The transducer side of each of the diode pairs is coupled to ground through a resister, denoted as Rm, the value of which is picked to match the impedance of the line 24 in each case. This matching ensures that the electrical form of the received echoes from the transducer 22 over the wire pair 24 are not partially reflected back out on to the transmission line creating multiple reflection patterns. In addition, the source impedance of the driver 30 should be chosen as close as possible to zero in order to effectively transmit the maximal amount of energy out to the transmission lines 24. The winding ratio of the transformer 94 in the present. embodiment is such to allow for approximately 75 volts peak-to-peak excitation signal for the transducer 22. The burst or pulse enveloping the excitation may be on the order of 1–8 microseconds with an inter-pulse period on the order of 2–4 milliseconds. This configuration of the drive circuit 30 allows for a balanced drive which tolerates a short on the primary side of the transformer 94, which won't be transferred to the secondary side to affect substantially the transducer 22 on the secondary side because of the DC isolation afforded by the tranformer. The configuration further maximizes energy transfer to the transducer 22 while preserving the common mode rejection ratio of the circuit.

The receiver circuit embodiment of FIG. 4 includes a differential amplifier 100 having its inverting (–) and non-inverting (+) inputs coupled to the resisters Rm through respective resisters 104 and 102. The amplifier 100 outputs to the interface circuit 26 and also to a phase determining circuit 106 which will be described in further detail hereinbelow.

In operation, an excitation signal from exciter 90 of approximately 1 megahertz in frequency is amplified by the amplifier 92 which drives the primary side of the transformer 94. Transformer 94 steps up the sinusoidal voltage to approximately 75 volts peak to peak and drives the transducer 22 through the balance diode pairs 95, 96 and 97, 98. Electrical echo signals from the transducer 22 are conducted over the lines 24 to the input of the differential amplifier 100 which amplifies the echo signals and conducts the amplified result to the interface circuit 26 which ultimately provides them to the processor 28 in a timed relationship to the incipient ultrasonic excitation pulse which is also conducted through the amplifier 100 to the interface 26 and processor 28.

The phase circuit 106 of the embodiment of FIG. 4 is important to the overall ultrasonic quantity gauging system by detecting the phase of a returning ultrasonic echo burst signal relative to the incipient transmit burst signal. It is well known that an ultrasonic burst reflection of a reflecting surface having a real acoustic impedance higher than the acoustic impedance of the media through which the ultrasonic burst signal is traveling, will reflect at 180 out of phase with the incipient burst signal. For example, this condition will occur when an ultrasonic burst echo is reflected off of a metallic velocity of sound target like those shown at 42 and 44 in the embodiment described in connection with FIG. 2. Therefore, the reflections 54 and 56 are expected to be 180 out of phase with the incipient signal 52. Likewise, when an ultrasonic burst echo reflects off of an interface where the real acoustic impedance of the interfacing material is less than the media in which the ultrasonic burst signal is traveling, it returns in phase with the incident ultrasonic burst signal. For example, this condition will occur at a fluid stratification boundary like that shown in FIG. 2 at 48 and also at the liquid height surface like that shown at 46 in FIG. 2. Accordingly, the ultrasonic burst echo signals 58 and 60 are expected to be in phase with the incipient burst signal 52. With this echo phase information as determined by the phase circuit 106, the gauging system can identify if an echo is returning from a fluid surface and/or fluid interface, or a velocity of sound target. Without this phase information of the echo burst signal, it is very difficult to discriminate between echo burst signals to determine the source of the echo signal in an ultrasonic quantity gauging system, especially a system containing stratified fuel and/or more than one velocity of sound target such as that described in connection with the embodiment of FIG. 2.

Figure 5:
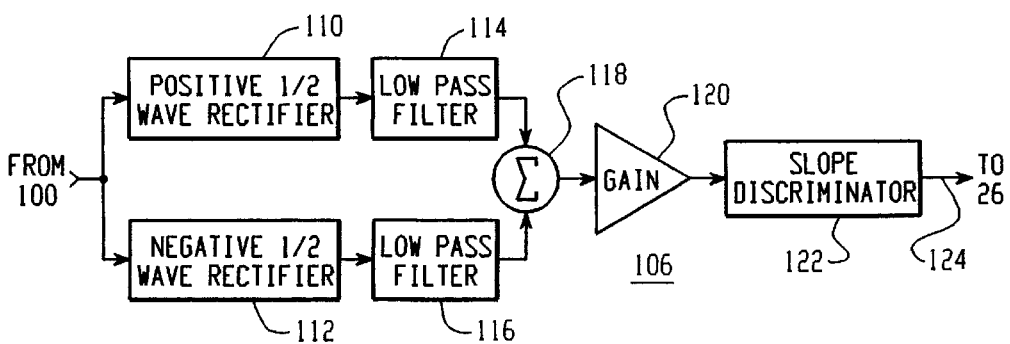
FIG. 5 is a block diagram schematic of a phase discriminator embodiment suitable for use in the embodiment in FIG. 2.

A block diagram schematic of a suitable phase circuit 106 is exemplified in FIG. 5. Referring to FIG. 5, the output signal of the amplifier 100 is conducted to both a positive one-half wave rectifier 110 and a negative one-half wave rectifier 112. The outputs of the rectifiers 110 and 112 are each passed though respective low pass filters 114 and 116, and summed in a sumer 118. The output of the sumer 118 is acted upon by a gain stage 120 before being conducted to a slope discriminator 122 which outputs a phase representative signal 124 to the interface circuit 26 and processor 28 for further processing.

Figure 6:
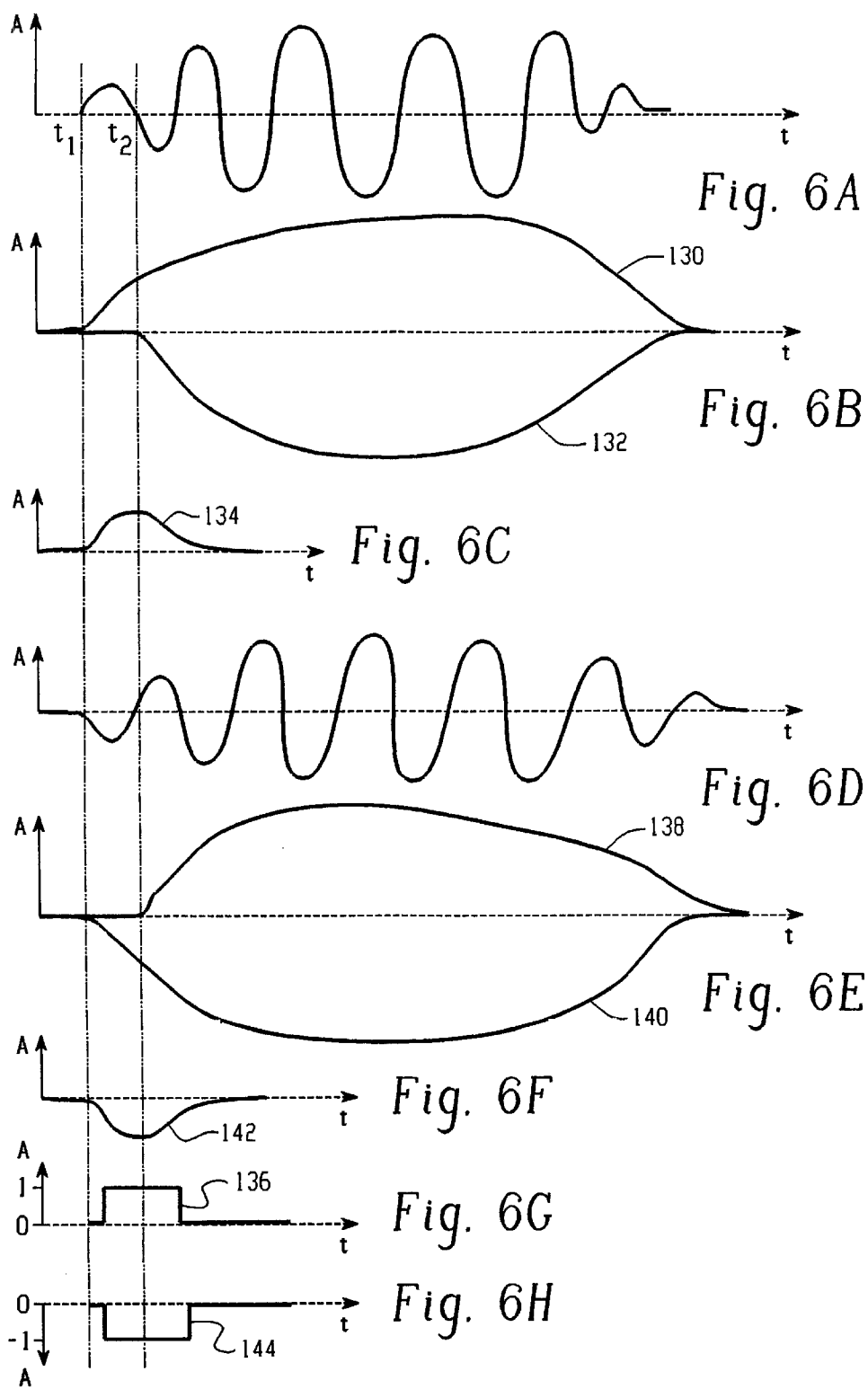
FIGS. 6A through 6H are time waveform illustrations for describing the operation of the phase discriminator embodiment of FIG. 5.

An operation of the phase circuit embodiment of FIG. 5 will now be described in connection with the time waveforms of FIGS. 6A through 6H. An example of an ultrasonic burst echo signal having a positive phase is shown in FIG. 6A. As this positive phase signal is passed through the positive one-half wave rectifier 110 and low pass filter 114, a positive envelope signal such as that shown at 130 in FIG. 6B is generated. Similarly, as the burst echo signal of FIG. 6A is passed through the rectifier 112 and filter 116, a negative envelope signal such as that shown at 132 in FIG. 6B is generated. Because the positive envelope signal was generated in time before the negative envelope signal from the corresponding echo signal, a short duration waveform signal like that shown at 134 in FIG. 6C is generated from the sumer 118 in the polarity direction of the phase of the burst echo signal. The positive going short duration waveform 134 is amplified in the gain circuit 120 so as when compared to a threshold level in the discriminator 122 a positive going pulse representative of phase will be generated over the signal line 124 similar to that shown at 136 in FIG. 6G.

Should the burst echo signal have a negative phase such as that shown FIG. 6D, it will pass through the positive and negative rectifiers 110 and 112 and corresponding filters 114 and 116, and result in the positive and negative envelope signals 138 and 140, respectively, illustrated in FIG. 6E. Note that for the negative phase burst echo signal of FIG. 6D the negative envelope signal was generated in time before the positive envelope signal therefrom. Because the negative envelope signal 140 was generated in time before the positive envelope signal 138, the resultant summation of 118 is a short waveform in the polarity direction of the negative phase similar to that shown at 142 of FIG. 6F. The signal 142 is amplified in the gain circuit 120 and compared to a threshold level in the discriminator 122 to yield a negative pulse over signal line 124 such as that shown at 144 in FIG. 6H to represent an echo having a negative phase. Accordingly, each burst echo signal and a signal representing its phase are provided to the interface circuit 26 and, in turn, the processor 28 which utilizes this information for discriminating between echo sources of the incipient ultrasonic burst signal transmitted from the ultrasonic transducer.

According to the embodiment described in connection with FIG. 2, examples of envelope response time waveforms of the incipient and echo burst signals are shown in FIG. 7. In this example, the incipient ultrasonic burst echo signal is shown initiating at time t0. Since, in the present embodiment, the processor 28 generates the incipient signal, it inherently knows the phase thereof and the time of initiation. At some time after t0, say t1, for example, the processor 28 receives an echo burst signal and a phase representative signal thereof from the receiver circuit 32 and interface 26. The processor 28 may compare the phases of the incipient and echo signal t1 and determine if the echo signal t1 is either in place or 180 out of phase with the incipient signal.

If the incipient burst signal at t0 is considered to have a positive phase characterized by a waveform with an initial positive slope and the echo signal at t1 has a negative phase characterized by a waveform with an initial negative slope, or vice-versa, the burst echo signal at t1 is determined to be 180 out of phase with the incipient signal and considered to be the echo signal 54 from the metal velocity of sound target 42. Thereafter, the processor 28 may receive another pulse at say time t2 and a phase representative signal thereof and determine from this information that the echo is in phase with the incipient transmission and therefore considered as being echo 58 from the stratification layer 48. Next, the processor 28 receives an echo signal at a later time t3 and utilizing the same discrimination process identifies this echo signal as coming from the second velocity of sound target 44. A later echo received by processor 28 at t4 is again discriminated by phase and determined to be in phase with the incipient burst transmission and therefore identified as the echo signal 60 reflected from the fuel height surface 46. Further echo signals may be received at t5, t6 and t7 which may result from secondary and tertiary reflections of the incipient ultrasonic transmitted pulse and of no consequence to the measurement of the liquid height in the tank 14.

Reference is now made to FIG. 8 which depicts a suitable circuit for embodying the phase circuit 106. In this embodiment, the signal from the amplifier 100 is conducted to one side of each capacitor C1 and C2 which decouple the DC component of the burst echo signal. As indicated previously, the frequency of the burst echo signal for the present embodiment may be on the order of one megahertz. At this frequency, the capacitors C1 and C2 may be on the order of 1500 picofarads each. After the echo signal passes through C1, it is conducted through a Schottky diode Z1 anode to cathode, and on to a non-inverting (+) input of an operational amplifier A1 wherein the non-inverting input being coupled to ground. The burst echo signal from C1 is also coupled through another Schottky diode Z2 to the inverting (−) input of the amplifier A1 and then through a parallel combination of resistor R1 and capacitor C3 to a node N1 which is coupled through a resistor R2 to the output of the amplifier A1. The node N1 is also coupled through a diode D1, cathode to anode, to ground and through capacitor C4 also to ground. In the present embodiment, the Schottky diodes Z1 and Z2 may each be of the type having model number 1N5711, the amplifier may be of the type manufactured by Analog Devices model no. AD827 and the diode D1 may be of the type bearing model no. 1N4148. Resistors R1 and R2 may have values on the order of 1.5 K ohms and 75 ohms and capacitors C3 and C4 may have values on the order of 3300 picofarads and 8200 picofarads, respectively.

The foregoing described circuitry embodies the positive one-half wave rectifier 110 and low pass filter 114. Similar circuitry is used for the negative one-half wave rectifier at 112 and low pass filter 116, except that the Schottky diodes Z1 and Z2 and diode D1 are reversed in conductivity. Other than that the components and values remain substantially the same. The difference in operation between the two circuits is such that a positive envelope signal is produced at N1 for the circuits 110 and 114 and a negative envelope signal is produced at node N2 for the negative rectifier and filter circuits 112 and 116. The positive and negative envelope signals are next buffered by operational amplifiers A3 and A4, respectively, each configured as a non-inverting unity gain amplifiers.

In the embodiment of FIG. 8, the positive and negative envelope signals are next coupled to an operational amplifier A5 configured as a summing amplifier wherein the positive and negative envelope signals are conducted respectively through resistors R3 and R4 to the inverting (−) input of amplifier A5 which includes a closed loop gain resistor R6 from input to output. The non-inverting input (+) of amplifier A5 is coupled to ground. In the present embodiment, R3 and R4 may be on the order of 1 K ohms and the resistor R6 may be on the order of 10 K ohms. The amplifiers A3, A4 and A5 may all be of the same type manufactured by Analog Devices model no. AD827, for example. The output of amplifier A5 which is an amplified summation signal is input to another operational amplifier circuit A6 which is configured as a comparator circuit, i.e. having a relatively high closed loop gain with the threshold set at ground reference level. The output of A5 is coupled through a resistor R7 to the inverting (−) input of amplifier A6 which is coupled through a feedback resistor R8 to the output thereof. The non-inverting (+) input of amplifier A6 is conducted to ground through a resistor R9. For the present embodiment, the values of the resistors R7, R8 and R9 may be on the order of 1 K ohms, 20 K ohms, and 900 ohms, respectively. The amplifier A6 may also be an Analog Device's AD827 operational amplifier.

In operation, the output of amplifier A6 generates a positive pulse as long as the output of A5 remains above ground level and generates a negative pulse as long as the output of A5 remains below ground level. It is understood that for the present embodiment ground level was chosen as the reference level, but other reference levels may be chosen for other embodiments. In addition, positive hysterisis may be provided around amplifier A6 to implement a window for positive and negative thresholds about ground and to mitigate transition oscillations at the output thereof.

Referring to FIG. 2, another aspect of the present invention involves a method of determining ultrasonically the height of a thermally stratified liquid in the tank 14 using at least one ultrasonic transducer 22 disposed at the bottom of the tank 14 for transmitting an ultrasonic signal 52 towards the height surface 46 of the liquid and for receiving ultrasonic reflections from at least two targets 42 and 44 at different predetermined heights from the bottom of the tank 14 and from the fuel height surface 46. The method includes measuring the temperature of the liquid at at least two different heights thereof. In the present embodiment, the temperature is measured at the bottom of the liquid (h=0) and at the surface of the liquid (h=1.0) utilizing the thermistors 36 and 34, respectively. The velocity of sound in the liquid at at least two different predetermined heights is determined using the reflections 54 and 56 of the targets 42 and 44 which are at the predetermined heights, h=0.3 and h=0.8 of the full liquid height or h=1.0. An approximation of velocity of sound versus temperature profile is established for the liquid in the tank which for the present embodiment is jet fuel A.

An approximation of velocity of sound versus height profile may be determined for each of a plurality of height regions based on the temperature measurements of thermistors 34 and 36 and the velocity of sound determinations of the different predetermined heights and the established approximation of velocity of sound versus temperature profile for the liquid in the tank 14. The time of the ultrasonic reflection 60 from the height surface 46 of the liquid is measured and the velocity of sound therefor is also determined based on the target ultrasonic reflection times and the velocity of sound verses height profile approximations. The height of the liquid may then be determined from the time measurement of the ultrasonic reflection from the height surface and the determined velocity of sound therefor. Accordingly, based on the foregoing described method, the number of velocity of sound verses height profile approximations determined is commensurate with the number of predetermined height velocity of sound determinations or in other words the number of target reflectors at different predetermined heights.

The exemplary embodiment described in connection with FIG. 2 provides for only two target reflectors 42 and 44, but it is certainly understood that additional target reflectors could be used yielding additional approximations of velocity of sound versus height profiles without deviating from the present invention. In addition, the established velocity of sound versus temperature profile approximation for the present embodiment is linear and based on the following expression:

$$V(T) = -B*T + K, \tag{1}$$

where

V(T) is the velocity of sound as a function of the liquid temperature, T,

B is predetermined based on the liquid in the tank,

K is a constant which may be approximated from measured liquid temperatures.

For the present embodiment the slope B was determined to be 4.475 which is a constant for all jet fuels. Further, while the temperature sensor measurement placements for the present embodiment were set at the bottom and top at the tank for convenience, it is understood that temperatures may be measured at different heights and include more than two.

Still further, the velocity of sound versus height profiles were approximated for each of two height regions, one going from the bottom of the tank to the first target reflector or height H1 and the other going from the first target reflector to the surface of the liquid or H=1.0. Each of these velocity of sound verses height profiles are linear for the present embodiment and based on the following expressions:

$$V1(h) = A1*h + C1,$$

for h greater than or equal to zero and less than or equal to H1, and $$V2(h) = A2*h + C2,$$

for h greater than or equal to H1 and less than or equal to 1.0, where the first height region extends from the bottom of the tank or h=0 to the first predetermined height or h=H1 and the second height region extends from H1 to the predefined maximum liquid height in the tank or h=1.0, and where V1(h) is the velocity of sound as a function of height for the first height region and V2(h) is the velocity of sound as a function of height for the second height region. In each case the velocity of sound V1(h) and V2(h) is the average or total integrated velocity of sound at the given height h.

Figure 9A:
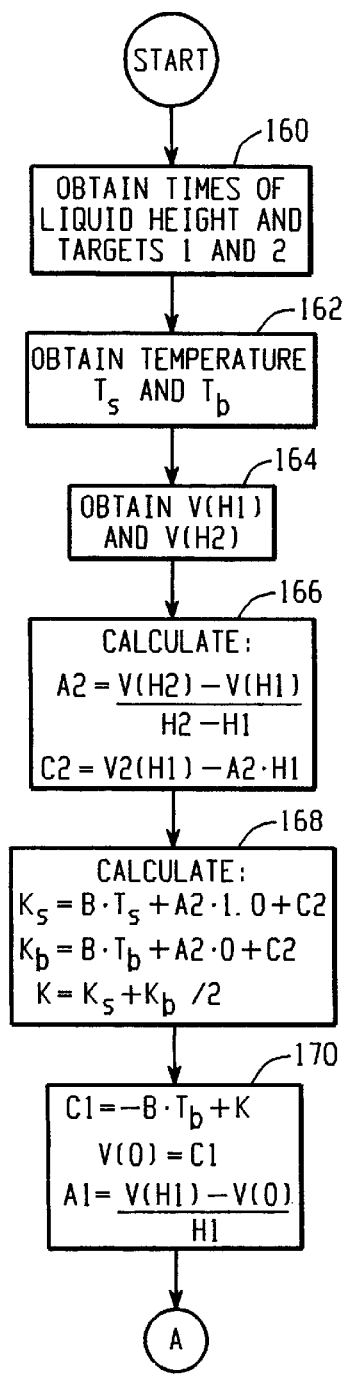
FIGS. 9A and 9B depict a flow chart suitable for use in programming the processor of the embodiment of FIG. 2 to perform a method of determining ultrasonically the height of a thermally stratified liquid in the tank thereof.

The method is embodied in the preferred ultrasonic liquid height gauging system as described in connection with FIG. 2 by programming a suitable algorithm into the processor 28 for execution therein. The flow charts of FIGS. 9A and 9B exemplify such a programmed algorithm. Starting with FIG. 9A, program execution starts at the program block 160 wherein the round trip times of the burst echo signals for the liquid height and velocity of sound of target reflectors 1 and 2 (42 and 44) are obtained. The process for obtaining the round trip reflection times, described in this application supra, and may be used for the programming block 160. Next in block 162, the temperature at the surface Ts and the bottom of the tank Tb are obtained from the thermistors 34 and 36, respectively. In the present embodiment, the value of the measured temperatures and times obtained from the blocks 160 and 162 may be stored in the memory of the processor 28. Next in block 164 the velocity of sound V(H1) at the first target reflector 42 at height H1 is obtained from the known predetermined distance Hi and the measured echo time obtained from the programming block 160. Likewise, the velocity of sound V(H2) is obtained at the target reflector 44 at the known predetermined height H2 thereof and the measured echo reflection time from block 160. As previously indicated for the present embodiment, the predetermined heights of target reflectors 42 and 44 are 0.30 and 0.80 of the full fuel height, respectively. With this knowledge and the measured reflection times, the velocity of sound for the two heights H1 and H2 are 1494.9 meters per second and 1454.2 meters per second, respectively.

Since we now have two points of a straight line, i.e. H1 and H2, for the velocity of sound versus height profile approximation for the second region, we can now determine the slope A2 and intercept C2 values thereof from the following expressions:

$$A2=(V(H2)-V(H1))/(H2-H1), \qquad (2)$$

$$C2=V2(H1)-A2*H1. \qquad (3)$$

Substituting the values 1454.2 meters per second for V(H2) and 1494.3 meters per second for V(H1), and 0.8 and 0.3 for H2 and H1 respectively, equation (2) yields minus 80.2. In addition, substituting −80.2 for A2 into equation (3) renders a value of C2 of 1518 meters per second. Accordingly, the velocity of sound verses height profile for the second height region thus becomes:
ti $V2(h)=-80.2*h+1518$ m/s, for h greater than 0.3 and less than or equal to 1.0.

Next in the program block 168, the program determines an approximation of the intercept K for the velocity of sound verses temperature profile of equation (1). Since it is known at any given height in the liquid the velocity of sound may be calculated by either the temperature profile or the height profile, equations (1) and (2) may be set equal. Still further, since the surface temperature Ts and bottom temperature Tb are measured and obtained in the programming block 162, then the intercept constant Ks for the surface and the intercept constant Kb for the bottom of the liquid may be determined by setting the equations (1) and (2) equal to one another. The resulting expressions are as follows:

$$Ks=-B*Ts+A2*1.0+C2,$$

and $$Kb=B*Tb+A2*0+C2.$$

In formulating the equation for Kb we are assuming that the velocity of sound verses height profile approximation for the second height region is valid for all heights in the tank. Thus, the known values can now be substituted into the equations for Ks and Kb resulting in the values of 1406.0 m/s and 1339.0 m/s, respectively. Since it is known that the value of Ks should be larger than the actual K and that the value of Kb should be smaller than the actual K, then the intercept K may be estimated by taking the average of the values of Ks and Kb. By substituting these values into an unweighted average equation the resulting value of block 168 for the intercept K becomes 1372.5 meters per second.

Accordingly, this approximation of K may be used as a first order approximation for the velocity of sound as a function of temperature in the tank for the given fuel. The velocity of sound as a function of temperature thus becomes:

$$V(T)=-4.475*T+1372.5 \text{ m/s}.$$

Next in the programming block 170, the intercept C1 and slope A1 for the velocity of sound verses height approximation of the first height region are determined. As indicated above, the velocity of sound at the bottom of the tank may be calculated either using the temperature profile or the height profile equations. Therefore, these equations may be set equal to each other. In addition, since the height is equal to zero at the bottom of the tank the term A2*h drops out of the equation and the resulting equation provides a value for C1:

$$C1=-B*Tb+K.$$

By substituting in the known values for B, Tb and K the value of C1 is determined to be 1551.5 meters per second. This value also is the velocity of sound V(0) at the bottom of the tank, i.e. h=0. Still further, the slope A1 of the velocity of sound verses height profile approximation for the first region becomes:

$$A1=(V(H1)-V(0))/H1.$$

By substituting in the known values for V(H1), V(0) and H1, the slope A1 becomes −191.87. Accordingly, the velocity of sound verses height profile approximation for the first region becomes:

$$V1(h)=-191.87*h+1551.5 \text{ m/s},$$

for h greater than or equal to zero and less than or equal to H1.

Figure 9B:
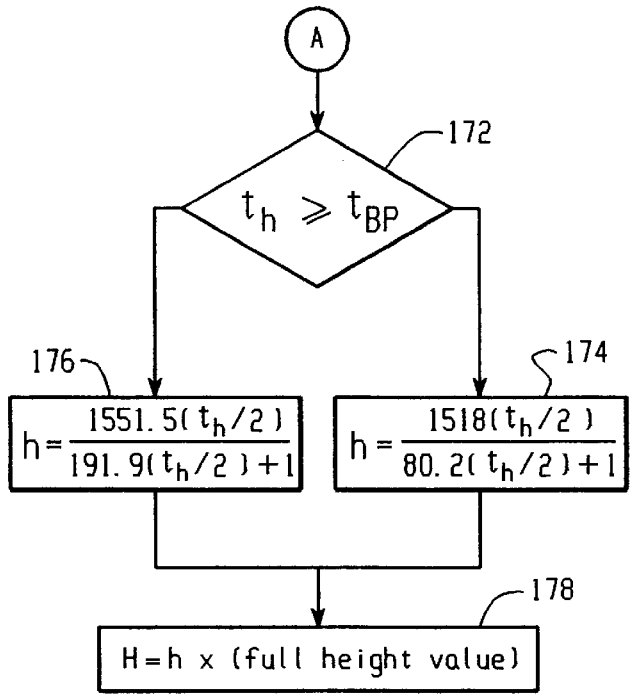

After obtaining the velocity of sound verses height profile approximations V1(h) and V2(h) for the two height regions, programming execution may continue over to the flow diagram of FIG. 9B wherein the liquid height is determined from the obtained liquid surface reflection or echo time $t_h$ and the appropriate velocity of sound versus height profile, V1(h) or V2(h). That is, $h=V1(h)*t_h/2$ or $V2(h)*t_h/2$. Note that the echo time $t_h$ is a round trip time value and is divided by two to establish the actual time to the liquid surface.

In block 172 of FIG. 9B, the appropriate equation V1(h) or V2(h) is determined by comparing echo time $t_h$ to a break point time $t_{BP}$ which may be determined from the following expression:

$$t_{BP}=(2*H1)/V(H1).$$

For the present embodiment, normalized H1=0.30 and V(H1)=1494.3 m/s; and therefore, $t_{BP}=(0.60/1494.3)$.

If $t_h$ is determined to be greater than or equal to $t_{BP}$ in block 172, then program execution is continued at block 174 wherein V2(h) is used to determine normalized liquid height h. Since V2(h) is a function of h, the equation $h=V2(h)*t_h/2$ is solved for h as follows:

$$h=(-80.2*h+1518)*t_h/2,$$

and thus $$h=(1518*t_h/2)/(80.2*(t_h/2)+1).$$

On the other hand, if $t_h$ is determined to be less than $t_{BP}$ then program execution continues at block 176 wherein V1(h) is used to determine normalized liquid height h. Since V1(h) is a function of h, the equation $h=V1(h)*t_h/2$ is solved for h as follows:

$$h=(-191.9*h+1551.5)*t_h/2,$$

and thus $h=(1551.5*t_h/2)/(191.9*(t_h/2)+1)$.

Once the normalized height value h is determined from either block 174 or 176, the actual height of the liquid in the tank is determined in block 178 by multiplying h by the full height value of the given tank in meters.

The foregoing described method for determining liquid height in a tank using the velocity of sound versus height profile approximations is suitable for accomplishing this function in the present embodiment, but it is understood that the velocity of sound versus height profiles as determined supra may be used in other methods, like sensor fusion and data fusion methods for determining liquid quantity in a tank, especially for an embodiment using a plurality of ultrasonic sensors and corrseponding target reflectors for each, without deviating form the scope and breadth of the appended claims. Such an embodiment is described in the copending U.S. patent application Ser. No. 08/996,858, entitled "Liquid Gauging Using Sensor and Data Fusion", filed on even date herewith, and assigned to the same assignee as the instant application, which application being incorporated by reference herein for providing a more detiled description thereof.

Figure 10:
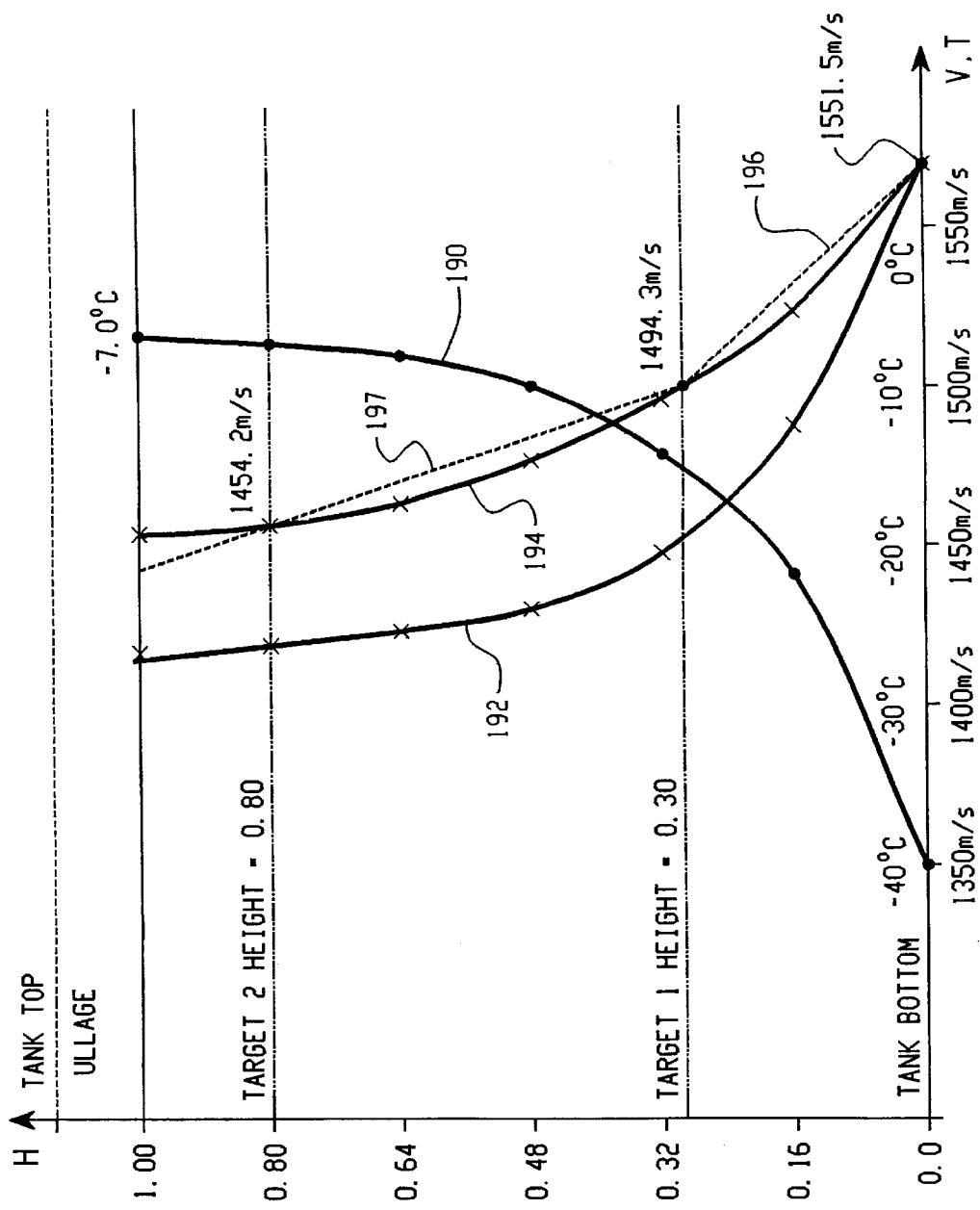
FIG. 10 is a graph depicting certain profile versus height curves established for a typical wing tank of an aircraft at one hour into flight for comparison purposes.

For comparison purposes certain profiles versus height were established for a typical wing tank of an aircraft that is full of type A aircraft fuel at one hour into a flight. The tank was equipped with sensors at heights 0.0, 0.16, 0.32, 0.48, 0.64, 0.80 and 1.0 of full fuel height. Accordingly, temperature and velocity of sound profiles verses height were measured under the aforementioned conditions. The graph of FIG. 10 depicts these profiles. The temperature verses height profile is shown in FIG. 10 by the solid line 190 and exhibits a temperature of −40 centigrade at the bottom of the tank and −7 centigrade at the fuel surface. The temperature verses height profile is parabolic as would be expected. In addition, the instantaneous velocity of sound verses height profile is depicted by the solid line 192 and the accumulative average velocity of sound verses height profile is depicted by the solid line 194 both of FIG. 10. Note that the velocity of sound in each case is 1551.5 meters per second at the bottom of the tank. Also, the accumulative average velocity of sound for the predetermined heights 0.30 and 0.80 are 1494.3 meters per second and 1454.2 meters per second, respectively. The aforementioned measured parameters were used in the inventive method to determined the velocity of sound verses height profile approximations shown by the dashed lines 196 for the first height region and dashed line 197 for the second height region. Accordingly, a comparison may be made between the piecewise linear approximations of 196 and 197 and the actual accumulative average velocity of sound of the solid line 194 in the graph of FIG. 4. Note that the approximations provide a good piece wise fit to the actual accumulative average velocity of sound profile in FIG. 10.

While the various aspects of the present invention have been described hereabove in connection with a particular embodiment, it is understood that such inventive aspects should not be limited to any such embodiment but rather construed in broad scope and breadth in accordance with the appended claims hereto.

We claim:

1. An ultrasonic transducer comprising:
 a layer of piezoresonator material having top and bottom surfaces and capable of transmitting from said top surface an ultrasonic pulse into a tank of liquid and receiving at said top surface reflections of said transmitted pulse from said liquid; and
 a matching layer of pure crystalline Boron Nitride disposed on the top surface of the piezoresonator layer, said ultrasonic pulse and reflections thereof conductible through said matching layer between the top surface of said piezoresonator layer and said tank liquid, said pure crystalline Boron Nitride layer operative to match the acoustic impedance of the piezoresonator material to the acoustic impedance of the tank liquid about the operational frequency passband of the ultrasonic pulse.

2. The transducer of claim 1 wherein the matching layer has a thickness of approximately one-quarter wavelength, which is based on the frequency of the ultrasonic pulse and the velocity of sound (VOS) through said matching layer material.

3. The transducer of claim 1 wherein the piezoresonator layer comprises a ceramic material.

4. The transducer of claim 3 wherein the ceramic material comprises lead zirconate titanate.

5. The transducer of claim 3 wherein the matching layer is bonded to the piezoresonator layer of ceramic material with an epoxy adhesive formulated for ceramic materials.

6. The transducer of claim 5 wherein the epoxy adhesive has a high temperature bonding rating which allows the bonding to withstand autoclave curing cycle temperatures.

7. The transducer of claim 1 wherein the pure crystalline Boron Nitride layer is grown by a pyrolytic chemical vapor deposition process.

8. The transducer of claim 1 wherein the matching layer is covered with at least one metal layer.

9. The transducer of claim 1 wherein the matching layer is covered with a layer of copper and a layer of chromium.

10. The transducer of claim 1 wherein the piezoresonator layer includes conductive layers on its top and bottom surfaces from which to connect lead wires.

11. The transducer of claim 10 wherein a finger of conductive material extends from the top surface to an electrically isolated conductive pad on the bottom surface of the piezoresonator layer from which to connect a lead wire.

12. The transducer of claim 10 wherein the top and bottom surfaces of the piezoresonator layer are plated with silver.

13. The transducer of claim 1 wherein the piezoresonator layer is operative to transmit the ultrasonic pulse with a narrow frequency passband centered substantially about one megahertz.

14. The transducer of claim 1 wherein the matching layer of pure crystalline Boron Nitride is the sole matching layer.

15. An ultrasonic transducer assembly for measuring a quantity of liquid in a container, said assembly comprising:
 a housing having top and bottom surfaces, said top surface for interfacing with the liquid of the container;
 an ultrasonic transducer disposed in said housing and comprising:
  a layer of piezoresonator material having top and bottom surfaces and capable of transmitting from said top surface an ultrasonic pulse into the container of liquid and receiving at said top surface reflections of said transmitted pulse from said liquid, said top and bottom surfaces of said piezoresonator layer covered with layers of conductive material; and
  a matching layer of pure crystalline Boron Nitride disposed on the top surface of the piezoresonator layer and configured as a window between said piezoresonator layer and said liquid at the top surface of said assembly, said ultrasonic pulse and reflections thereof conductible through said matching layer between the top surface of said piezoresonator layer and said liquid, said matching layer operative to match the acoustic impedance of the piezoresonator material to the acoustic impedance of said liquid about the operational frequency passband of the ultrasonic pulse, a surface of said matching layer at the liquid interface being covered with at least one metal layer;

a lead wire for each surface of said piezoresonator layer connected at one end to said conductive material layer thereof, said lead wires connectable at the other ends to a transducer driver/receiver circuit.

16. The transducer assembly of claim 15 wherein the matching layer is a sole matching layer.

17. The transducer assembly of claim 15 wherein the housing is hermetically sealed.

18. The transducer assembly of claim 15 wherein the piezoresonator layer comprises a ceramic material; and the matching layer is bonded to the piezoresonator layer by an epoxy adhesive formulated for ceramic materials.

19. The transducer assembly of claim 15 wherein the surface of the matching layer at the liquid interface is cover with layers of copper and chromium.

20. The transducer assembly of claim 15 including an hermetic header affixed at the bottom surface of the housing, said header including openings for extending the transducer lead wires from the housing.

21. The transducer assembly of claim 15 wherein the at least one metal layer of the matching window layer is affixed to the top surface of the housing.

22. The transducer assembly of claim 15 wherein the housing comprises an Invar material.

23. The transducer assembly of claim 22 wherein the Invar housing is tinned at the top surface; and wherein the at least one metal layer of the matching window layer is soldered to the tinned top surface of the housing to form a seal.

24. The transducer assembly of claim 22 including an hermetic header; and wherein the Invar housing is tinned at the bottom surface; and wherein the hermetic header is soldered to the tinned bottom surface of the housing to form a seal, said header including sealable openings for extending the transducer lead wires from the housing.

25. The transducer assembly of claim 15 wherein the housing is configured as a truncated pyramid.

26. The transducer assembly of claim 15 embeddable in a skin of an aircraft fuel tank, said skin comprising a composite material.

27. The transducer assembly of claim 26 wherein the assembly is capable of withstanding the curing temperatures of the composite material in which it is embeddable during said curing process.

* * * * *

UNITED STATES PATENT AND TRADEMARK OFFICE
CERTIFICATE OF CORRECTION

PATENT NO.     : 6,536,275 B1
DATED          : March 25, 2003
INVENTOR(S)    : Durkee, Scott Robert et al.

It is certified that error appears in the above-identified patent and that said Letters Patent is hereby corrected as shown below:

Title page,
After Item [22], the following should be inserted:
--          Related U.S. Application Data
[63] Continuation-in-part of application No. 08/996,747,
      filed on December 23, 1997, now abandoned. --

Column 17,
Line 62, after the words "An ultrasonic transducer", insert -- for measuring a quantity of liquid in a tank, said transducer --;
Line 65, "a" should read -- the --.

Signed and Sealed this

Twenty-eighth Day of October, 2003

JAMES E. ROGAN
*Director of the United States Patent and Trademark Office*